United States Patent
Hossain (10) Patent No.: US 11,224,636 B2
(45) Date of Patent: Jan. 18, 2022

(54) SUPER-OXIDE DISMUTASE SOLUBLE FIBER COMPOSITIONS

(71) Applicant: ADVANCE PHARMACEUTICAL, INC., Holtsville, NY (US)

(72) Inventor: Liaquat Hossain, Holtsville, NY (US)

(73) Assignee: ADVANCE PHARMACEUTICAL, INC., Holtsville, NY (US)

( * ) Notice: Subject to any disclaimer, the term of this patent is extended or adjusted under 35 U.S.C. 154(b) by 0 days.

(21) Appl. No.: 16/897,775

(22) Filed: Jun. 10, 2020

(65) Prior Publication Data

US 2020/0390867 A1 Dec. 17, 2020

Related U.S. Application Data

(60) Provisional application No. 62/992,459, filed on Mar. 20, 2020, provisional application No. 62/860,214, filed on Jun. 11, 2019.

(51) Int. Cl.

| *A61K 38/44* | (2006.01) |
| *A61K 47/36* | (2006.01) |
| *A61P 31/14* | (2006.01) |
| *A61K 47/46* | (2006.01) |
| *A23L 2/385* | (2006.01) |
| *A23L 2/08* | (2006.01) |
| *A23L 33/22* | (2016.01) |
| *A23L 33/105* | (2016.01) |
| *A61K 9/06* | (2006.01) |

(52) U.S. Cl.
CPC .............. *A61K 38/446* (2013.01); *A23L 2/08* (2013.01); *A23L 2/385* (2013.01); *A23L 33/105* (2016.08); *A23L 33/22* (2016.08); *A61K 9/06* (2013.01); *A61K 47/36* (2013.01); *A61K 47/46* (2013.01); *A61P 31/14* (2018.01); *C12Y 115/01001* (2013.01); *A23V 2002/00* (2013.01)

(58) Field of Classification Search
CPC .......... A23L 2/08; A23L 2/385; A23L 33/105; A23L 33/22; A23L 29/06; A23L 29/212; A23L 29/262; A23L 29/269; A23L 2/02; A23L 33/21; A23V 2002/00; A61K 38/446; A61K 47/36; A61K 47/46; A61K 9/06; A61P 31/14; C12Y 115/01001
See application file for complete search history.

(56) References Cited

U.S. PATENT DOCUMENTS

| 5,082,856 A * | 1/1992 | Taniguchi ............ C07D 207/34 514/423 |
| 5,925,363 A * | 7/1999 | Colin ...................... A61Q 5/10 424/401 |
| 7,241,461 B2 | 7/2007 | Myhill et al. |
| 10,946,075 B1 * | 3/2021 | Paxton-Pierson .... A61K 9/0014 |
| 2005/0112174 A1 | 5/2005 | Hermann |
| 2008/0020071 A1 | 1/2008 | Diaz |
| 2009/0074860 A1 * | 3/2009 | Borba ..................... A23L 33/15 424/464 |
| 2009/0226409 A1 * | 9/2009 | Calenda .................... A61P 9/10 424/94.4 |
| 2009/0258109 A1 * | 10/2009 | Ortiz De Zarate ...... A23G 3/42 426/5 |
| 2009/0263367 A1 * | 10/2009 | Foley ................... A61K 31/352 424/94.4 |
| 2010/0021533 A1 | 1/2010 | Mazed et al. |
| 2012/0308619 A1 * | 12/2012 | Tousley ................. A45D 44/22 424/401 |
| 2013/0295066 A1 | 11/2013 | Naidu et al. |
| 2015/0197580 A1 * | 7/2015 | Wang ...................... A23L 27/21 536/103 |
| 2015/0366256 A1 * | 12/2015 | Book ...................... A23L 15/20 426/298 |
| 2015/0374739 A1 * | 12/2015 | Ritter ................... A61K 35/741 424/456 |
| 2016/0015065 A1 * | 1/2016 | Sumner .................... A23L 33/20 426/590 |
| 2016/0106690 A1 * | 4/2016 | Bucks .................. A61K 9/0014 514/162 |
| 2016/0249655 A1 * | 9/2016 | Jung ........................ A23L 33/40 426/392 |
| 2016/0375014 A1 * | 12/2016 | Bosse ..................... A61K 45/06 424/472 |
| 2017/0119828 A1 * | 5/2017 | Nakamura ........... A61K 35/745 |
| 2017/0258115 A1 * | 9/2017 | Catani ....................... A23L 2/60 |
| 2018/0333448 A1 * | 11/2018 | Shen ...................... A61K 36/48 |
| 2019/0110981 A1 * | 4/2019 | Weimann ............... A61K 9/006 |

OTHER PUBLICATIONS

Vouldoukis et al. Phytotherapy Res. (2004) 18: 957-862 (Year: 2004).*
Takayanagi et al. Pharmacometrics (Oyo Yakuri) (2016) 90(5/6): 77-81 (Year: 2016).*
Machine Translation for CN 200910152680 published 2009 downloaded from EPO. (Year: 2009).*
Okada et al., Prevention of Inflammation-mediated acquisition of metastatic properties of benign mouse fibrosarcoma cells by administration of an orally available superoxide dismutase, British Journal of Cancer 94:854-862 (2006).
Spychalla et al., Superoxide Dismutase, Catalase, and alpha-Tocopherol Content or Stored Potato Tubers, Plant Physiol. 94:1214-1218 (1990).
Gopal et al., Industrial Production of Superoxide Dismutase (SOD): A Mini Review, J. Prob. Health, 5:3, 1000179 (2017).
International Search Report dated Sep. 16, 2020 for international application No. PCT/US202/037035.
McCord et al., An Enzymic Function for Erythrocuprein (Hemocuprein), J. Biol. Chem, 244:6049-6055, 1969.
Weydert et al., Measurement of superoxide dismutase, catalase and glutathione peroxidase in cultured cells and tissue, Nature Protocols, 5(1): 51-66, 2010.

(Continued)

*Primary Examiner* — Susan M Hanley
(74) *Attorney, Agent, or Firm* — Medler Ferro Woodhouse & Mills PLLC (57) ABSTRACT

Provided are compositions comprising super-oxide dismutase and a soluble fiber. The compositions may additionally comprise other antioxidants, vitamins and nutrients. The compositions can be used as dietary supplements and for improving health and well-being.

34 Claims, 1 Drawing Sheet

(56) References Cited

OTHER PUBLICATIONS

Technical Protocol "Enzymatic Assay of Superoxide Dismutase," retrieved from https://www.sigmaaldrich.com/technical-documents/protocols/biology/enzymatic-assay-of-superoxide-dismutase.html.

Gupta et al., Methods for Measuring Oxidative Stress in the Laboratory, Chapters (pp. 19-40) of Antioxidants in Food, Vitamins and Supplements (Elsevier), 2014.

Vouldoukis et al., Antioxidant and anti-inflammatory properties of a Cucumis melo LC. extract rich in superoxide dismutase activity, J. Ethnopharmacology, 94:67-75, 2004.

Amir, "Soluble Corn Fiber: Corn Fiber Facts and is It Keto?" published at perfectketo.com/soluble-corn-fiber/ on Feb. 19, 2021.

"Food Sources of Soluble Fibre," published by Dietitians of Canada, updated Mar. 16, 2013.

"Scientific Opinion on the substantiation of health claims related to superoxide dismutase (SOD) and protection of DNA, proteins and lipids from oxidative damage (ID 1785, 1839, 1970, 2304, 2305, 3159, 3160), protection of the skin from photo-oxidative (UV-induced) damage (ID 2305, 3161), reduction of muscle fatigue during exercise (ID 1840), and "effects on immune system" (ID 2304, 3160) pursuant to Article 13(1) of Regulation (EC) No. 1924/20061," EFSA Journal 8(10):1754, 2010.

* cited by examiner

SUPER-OXIDE DISMUTASE SOLUBLE FIBER COMPOSITIONS

FIELD OF THE INVENTION

The present disclosure relates generally to compositions comprising super-oxide dismutase and a soluble fiber. The compositions can be used as dietary supplements and for improving health and well-being.

BACKGROUND OF THE INVENTION

Superoxide dismutases (SODs) are a group of metalloenzymes that protect against cellular damage by reactive oxygen species (ROS). SOD catalyzes the dismutation of superoxide anion free radical (O) into molecular oxygen and hydrogen peroxide ($H_2O_2$). ROS in cells can damage nucleic acids, proteins and lipids leading to decreased cellular function and possible apoptosis. Thus, the ability to convert ROS into harmless molecules is crucial for protecting cellular function and overall health.

While almost all organisms naturally produce some type of SOD, the levels of SOD produced in cells falls as the subject ages or when the subject is afflicted with certain health disorders. Also, the presence of various pollutants and toxins in the environment can cause increased levels of ROS in cells. Dietary supplementation of naturally produced SOD can therefore be important to maintaining health.

Another important dietary component is soluble fiber. Soluble fiber absorbs water and forms a gel in the digestive tract. Soluble fiber has many benefits in the gut, including slowing the digestion of certain types of lipids and carbohydrates, helping to prevent uptake of dietary cholesterol and prevent spikes in blood sugar levels. Soluble fiber is also important for maintaining a health gut microbiome, as gut bacteria can ferment some types of soluble fiber. Modern diets are typically low in soluble fiber and supplementation is often needed for improved health.

Diabetes mellitus (diabetes) is a common disorder of carbohydrate metabolism. In the US more than 30 million people have diabetes. In the last 20 years, the number of adults diagnosed with diabetes has more than tripled as the American population has aged and become more overweight or obese. In people who have diabetes, the normal ability of the body to utilize glucose is compromised, leading to increased blood glucose levels. Diabetes is associated with enhanced risks of cardiovascular or circulatory diseases or disorders.

Fiber, such as soluble fiber, in food has been shown to blunt the glycemic response to a meal. When fermented by gut bacteria, fiber also produces metabolites of Short Chain Fatty Acids [SCFAs] that participate in glucose homeostasis. However, high fiber food can cause stomach discomfort as can certain fiber supplements.

Antioxidants have been shown to have beneficial effects in the human body in combating free radicals, which are involved in many disease processes. However, the absorption of the effective metabolites of many antioxidants, such as polyphenols, depends on microbial metabolism of the antioxidants in the gut. Thus, for many nutritional supplements, these effective polyphenol metabolites are not produced and the antioxidant activity the supplement is limited.

BRIEF SUMMARY OF THE INVENTION

The present disclosure is directed to a composition comprising from about 0.5 units/mg to about 500 units/mg superoxide dismutase and a soluble fiber. In some embodiments of the disclosure, the composition comprises from about 1 units/mg to about 100 units/mg superoxide dismutase. In some embodiments of the disclosure, the composition comprises from about 5 units/mg to about 50 units/mg superoxide dismutase. In some embodiments of the disclosure, the composition comprises from about 10 units/mg to about 15 units/mg superoxide dismutase. In some embodiments of the disclosure, the composition comprises about 14 units/mg superoxide dismutase.

In some embodiments of the disclosure, the superoxide dismutase in the composition is extracted from melon, bovine liver, heterotrophic bacteria or marine phytoplankton. In some embodiments of the disclosure, the superoxide dismutase is a copper/zinc superoxide dismutase, an iron/manganese superoxide dismutase or a nickel superoxide dismutase.

In some embodiments of the disclosure, the superoxide dismutase in the composition is extracted from a plant. In some embodiments, the plant is a fruit, a grain or a tuber. In some embodiments, the plant is a fruit selected from melon, citrus fruit, peach, pear, apple or banana. In some embodiments, the plant is a grain selected from wheat, barley, rye, millet, oat, spelt, bulger, sorghum and farro. In some embodiments, the plant is a tuber selected from horseradish, potato, yam, sweet potato, cassava or dahlia.

In some embodiments of the disclosure, the superoxide dismutase in the composition is extracted from an animal. In some embodiments, the animal is a cow, pig, sheep or goat.

In some embodiments of the disclosure, the superoxide dismutase in the composition is extracted from a microorganism. In some embodiments, the microorganism is phytoplankton or bacteria.

In some embodiments of the disclosure, the ratio of superoxide dismutase to soluble fiber in the composition is from about 1:100 to about 1:1000 by weight. In some embodiments of the disclosure, the ratio of superoxide dismutase to soluble fiber in the composition is from about 1:200 to about 1:800 by weight. In some embodiments of the disclosure, the ratio of superoxide dismutase to soluble fiber in the composition is from about 1:300 to about 1:700 by weight. In some embodiments of the disclosure, the ratio of superoxide dismutase to soluble fiber in the composition is from about 1:500 to about 1:700 by weight. In some embodiments of the disclosure, the ratio of superoxide dismutase to soluble fiber in the composition is from about 1:650 to 1:675 by weight.

In some embodiments of the disclosure, the soluble fiber in the composition is a water soluble polysaccharide. In some embodiments of the disclosure, the soluble fiber in the composition is isolated from corn, wheat, barley, rye, beans, apples, pears, peaches, citrus fruits, berries, peas, rice bran or oats. In some embodiments of the disclosure, the soluble fiber in the composition is selected from soluble corn fiber, inulin, dextrin, Guar gum, oligopolysaccharides, galactopolysaccharides fructo-oligosaccharides, lactulose, digestion-resistant starch, xylo-oligosaccharides and isomelto-oligossacharides. In some embodiments of the disclosure, the soluble fiber in the composition is soluble corn fiber. In some embodiments of the disclosure, the soluble fiber in the composition is digestion-resistant maltodextrin.

In some embodiments of the disclosure, the composition is in the form of a powder. In some embodiments, the powder composition comprises from about 0.1 ppm to about 10 ppm superoxide dismutase by weight. In some embodiments, the powder composition comprises from about 0.5 ppm to about 5 ppm superoxide dismutase by weight. In some embodiments, the powder composition comprises from about 0.7 ppm to about 2 ppm superoxide dismutase by weight. In some embodiments, the powder composition comprises from about 0.8 ppm to about 1.2 ppm superoxide dismutase by weight. In some embodiments, the powder composition comprises from about 1% to about 90% soluble fiber by weight. In some embodiments, the powder composition comprises from about 1% to about 50% soluble fiber by weight. In some embodiments, the powder composition comprises from about 5% to about 25% soluble fiber by weight. In some embodiments, the powder composition comprises from about 10% to about 20% soluble fiber by weight. In some embodiments, the powder composition comprises from about 12% to about 14% soluble fiber by weight.

In some embodiments of the disclosure, the composition is in the form of a gel. In some embodiments of the disclosure, the composition is in the form of a liquid. In some embodiments, the gel or liquid composition comprises from about 0.005 mg/mL to about 3.0 mg/mL superoxide dismutase. In some embodiments, the gel or liquid composition comprises from about 0.01 mg/mL to about 2.0 mg/mL superoxide dismutase. In some embodiments, the gel or liquid composition comprises from about 0.05 mg/mL to about 1.0 mg/mL superoxide dismutase. In some embodiments, the gel or liquid composition comprises from about 0.1 mg/mL to about 0.5 mg/mL superoxide dismutase.

In some embodiments, the gel or liquid composition comprises from about 50 mg/mL to about 1000 mg/mL soluble fiber. In some embodiments, the gel or liquid composition comprises from about 70 mg/mL to about 500 mg/mL soluble fiber. In some embodiments, the gel or liquid composition comprises from about 90 mg/mL to about 250 mg/mL soluble fiber. In some embodiments, the gel or liquid composition comprises from about 100 mg/mL to about 200 mg/mL soluble fiber.

In some embodiments of the disclosure, the composition comprising superoxide dismutase and soluble fiber also comprises a fruit juice. In some embodiments, the fruit juice is pomegranate juice, red grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice, prune juice or combinations thereof. In some embodiments, the fruit juice is concentrated pomegranate juice, red grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice, prune juice or combinations thereof. In some embodiments, the concentrated fruit juice has about 60% to about 97% of the water of the juice removed. In some embodiments, the concentrated fruit juice has about 85% to about 95% of the water of the juice removed. In some embodiments, the composition comprises from about 5 mg/mL to about 200 mg/mL of the concentrated fruit juice. In some embodiments, the composition comprises from about 75 mg/mL to about 150 mg/mL concentrated pomegranate juice. In some embodiments, the composition comprises from about 75 mg/mL to about 150 mg/mL concentrated red grape juice. In some embodiments, the composition comprises from about 25 mg/mL to about 100 mg/mL concentrated blueberry juice. In some embodiments, the composition comprises from about 20 mg/mL to about 80 mg/mL concentrated dark sweet cherry juice. In some embodiments, the composition comprises from about 20 mg/mL to about 80 mg/mL concentrated sour cherry juice. In some embodiments, the composition comprises from about 2 mg/mL to about 20 mg/mL concentrated goji berry juice. In some embodiments, the composition comprises from about 2 mg/mL to about 20 mg/mL concentrated acai berry juice.

In some embodiments of the disclosure, the composition comprising superoxide dismutase and soluble fiber also comprises aloe vera. In some embodiments, the aloe vera is concentrated aloe vera. In some embodiments, the concentrated aloe vera has about 60% to about 97% of the water of the aloe vera removed. In some embodiments, the composition comprises from about 2 mg/mL to about 20 mg/mL concentrated aloe vera.

In some embodiments of the disclosure, the composition comprising superoxide dismutase and soluble fiber also comprises green tea. In some embodiments, the green tea is concentrated green tea. In some embodiments, the concentrated green tea is a green tea extract. In some embodiments, the composition comprises from about 2 mg/mL to about 20 mg/mL concentrated green tea.

In some embodiments of the disclosure, the composition comprising superoxide dismutase and soluble fiber also comprises resveratrol. In some embodiments, the composition comprises from about 0.5 mg/mL to about 6 mg/mL resveratrol.

In some embodiments of the disclosure, the gel composition comprising superoxide dismutase and soluble fiber also comprises carboxymethyl cellulose. In some embodiments, the composition comprises from about 0.5 to about 5.0 mg/mL carboxymethyl cellulose.

In some embodiments of the disclosure, the gel composition comprising superoxide dismutase and soluble fiber also comprises xanthan gum. In some embodiments, the composition comprises from about 0.5 to about 5.0 mg/mL xanthan gum.

The present disclosure is also directed to a composition comprising: a) from about 0.5 units/mg to about 100 units/mg superoxide dismutase; b) a soluble fiber; and c) at least two fruit juices selected from pomegranate juice, red grape juice, blueberry juice, dark sweet cherry juice, sour cherry juice, goji berry juice and acai berry juice. In some embodiments, the composition comprises at least three fruit juices. In some embodiments, the composition comprises at least four fruit juices. In some embodiments, the composition comprises at least five fruit juices. In some embodiments, the composition comprises at least six fruit juices. In some embodiments, the composition comprises pomegranate juice, red grape juice, blueberry juice, dark sweet cherry juice, sour cherry juice, goji berry juice and acai berry juice.

In some embodiments of the composition, the fruit juices are concentrated fruit juices. In some embodiments of the composition, the soluble fiber is soluble corn fiber. In some embodiments, the soluble corn fiber is digestion-resistant maltodextrin.

The present disclosure is also directed to a composition comprising: a) superoxide dismutase; b) a soluble corn fiber; c) at least two fruit juices selected from pomegranate juice, red grape juice, blueberry juice, dark sweet cherry juice, sour cherry juice, goji berry juice and acai berry juice; d) aloe vera; e) green tea; and f) resveratrol. In some embodiments, the composition comprises at least three fruit juices. In some embodiments, the composition comprises at least four fruit juices. In some embodiments, the composition comprises at least five fruit juices. In some embodiments, the composition comprises at least six fruit juices. In some embodiments, the composition comprises pomegranate juice, red grape juice, blueberry juice, dark sweet cherry juice, sour cherry juice, goji berry juice and acai berry juice.

In some embodiments of the composition, the fruit juices are concentrated fruit juices. In some embodiments of the composition, the soluble corn fiber is digestion-resistant maltodextrin. In some embodiments, the composition also comprises carboxymethylcellulose. In some embodiments, the composition also comprises xanthan gum.

The present disclosure is also directed to a composition comprising: a) from about 30 units to about 1000 units superoxide dismutase; b) from about 50 mg/mL to about 200 mg/mL of a soluble corn fiber; c) from about 5 mg/mL to about 200 mg/mL each of at least two concentrated fruit juices selected from pomegranate juice, red grape juice, blueberry juice, dark sweet cherry juice, sour cherry juice, goji berry juice and acai berry juice; d) from about 2 mg/mL to about 20 mg/mL concentrated aloe vera; e) from about 2 mg/mL to about 20 mg/mL concentrated green tea; and f) from about 0.5 mg/mL to about 6 mg/mL resveratrol.

In some embodiments of the composition, the soluble corn fiber is digestion-resistant maltodextrin. In some embodiments, the composition also comprises about 0.5 to about 5.0 mg/mL carboxymethyl cellulose. In some embodiments, the composition also comprises from about 0.5 to about 5.0 mg/mL xanthan gum.

In embodiments of any of the compositions disclosed herein, the composition has an oxygen radical absorbance capacity (ORAC) of greater than 1000 µmol/g of the composition. In embodiments of any of the compositions disclosed herein, the composition has an ORAC of greater than 1500 µmol/g of the composition. In embodiments of any of the compositions disclosed herein, an ORAC value for the composition is at least 1.5 fold higher than the sum of individual ORAC values for each component of the composition. In embodiments of any of the compositions disclosed herein, an ORAC value for the composition is at least 1.6 fold higher than the sum of individual ORAC values for each component of the composition.

The present disclosure is further directed to a method of reducing the number of free oxygen radicals in a mammal, comprising administering to the mammal any of the compositions disclosed herein. In some embodiments of the method, the free oxygen radicals to be reduced in number are peroxyl radicals, hydroxyl radicals, peroxynitrite, superoxide anion, singlet oxygen, hypochlorite or combinations thereof.

The present disclosure is further directed to a method of reducing inflammation in a mammal, comprising administering to the mammal any of the compositions disclosed herein.

The present disclosure is further directed to a method of reducing viral symptoms in a mammal, comprising administering to the mammal any of the compositions disclosed herein.

In embodiments of the methods disclosed herein, the composition is administered to the mammal once a day. In embodiments of the methods disclosed herein, the composition is administered to the mammal twice a day. In embodiments of the methods disclosed herein, the mammal is a human.

DETAILED DESCRIPTION OF THE INVENTION

The present disclosure provides compositions comprising superoxide dismutase and a soluble fiber. The compositions disclosed herein can be used as supplements to increase the levels of superoxide dismutase and soluble fiber in subject. As described herein, the compositions can also comprise additional components such as antioxidants, vitamins or other nutrients along with excipients and other formulation agents.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict from any reference cited herein and the specific teachings of this specification shall be resolved in favor of the latter. Likewise, any conflict from an art-understood definition of a word or phrase and a definition of the word or phrase as specifically taught in this specification shall be resolved in favor of the latter.

As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability, depending on the situation.

The use of the term "or" in the claims is used to mean "and/or", unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

Technical and scientific terms used herein have the meaning commonly understood by one of skill in the art to which the present application pertains, unless otherwise defined. Reference is made herein to various methodologies and materials known to those of skill in the art.

The term "superoxide dismutase" (sometimes abbreviated SOD) as used herein refers an enzyme that catalyzes the dismutation of superoxide anion free radical ($O_2^-$) into molecular oxygen and hydrogen peroxide ($H_2O_2$). Superoxide dismutase has the Enzyme Classification (EC) number 1.15.1.1. Superoxide dismutase is an important component in protecting cells against damage from reactive oxygen species (ROS) such as $O_2^-$ that are formed during cellular metabolism of oxygen. Superoxide dismutase thus acts as an important antioxidant and is present in almost all types of cellular organisms. However, particularly in complex organisms such as mammals, cellular levels of superoxide dismutase decrease as the organism ages, making the organism more susceptible to cellular damage from reactive oxygen species.

The term "soluble fiber" as used herein refers to any type of water soluble dietary fiber. When consumed, soluble fiber absorbs water to form a gel in the gut of the organism that helps to slow the metabolism of lipids and carbohydrates. Soluble fiber is also a pre-biotic that can be fermented by gut bacteria which helps maintain a healthy gut microbiome.

The term "antioxidant" as used herein refers to a substance that significantly decreases the adverse effects of reactive species, such as reactive oxygen and nitrogen species by wholly or partially neutralizing reactive species. Antioxidants can be classified as "primary antioxidants" and "secondary antioxidants." Primary antioxidants delay or inhibit the initiation step of oxidation, while secondary antioxidants slow down the oxidation by removing the substrate or by quenching free oxygen radicals.

Superoxide Dismutase and Soluble Fiber

The embodiments, the compositions disclosed herein comprise an amount of superoxide dismutase as measured in units of activity per mg of protein. For enzyme activity, one unit (U) (expressed in μmol/min) is defined as the amount of the enzyme that catalyzes the conversion of one micromole of substrate per minute under specified conditions. The units of superoxide dismutase activity can be measured by any known method. For example, methods of determining superoxide dismutase activity in units are described in McCord, J. M. and Fridovich, I., *J. Biol. Chem.* 1969, 244:6049-6055; Weydert et al., *Nature Protocols* 2010, 5(1): 51-66; and in the technical protocol at https://www.sigmaaldrich.com/technical-documents/protocols/biology/enzymatic-assay-of-superoxide-dismutase.html; the disclosures of each of which are incorporated by reference herein. In embodiments, a unit of superoxide dismutase activity is defined as the amount of superoxide dismutase that will inhibit the rate of reduction of cytochrome c by 50% in a coupled system, using xanthine and xanthine oxidase at pH 7.8 at 25° C. in a 3.0 ml reaction volume.

In embodiments, the compositions disclosed herein comprise from high concentrations of superoxide dismutase, e.g., greater than 0.5 units/mg, greater than 0.1 units/mg, greater than 1 units/mg, greater than 10 units/mg, greater than 50 units/mg, greater than 100 units/mg, greater than 200 units/mg, greater than 500 units/mg, greater than 1000 units/mg, greater than 2000 units/mg, greater than 2500 units/mg, greater than 3000 units/mg, greater than 4000 units/mg or greater than 5000 units/mg superoxide dismutase, and a soluble fiber. In embodiments, the compositions disclosed herein comprise from about 5 units/mg to about 5000 units/mg, from about 5 units/mg to about 4000 units/mg, from about 5 units/mg to about 3000 units/mg or from about 5 units/mg to about 2000 units/mg superoxide dismutase and a soluble fiber. In embodiments, the compositions comprise from about 1 unit/mg to about 1000 units/mg, from about 1 unit/mg to about 750 units/mg, from about 1 unit/mg to about 500 units/mg, or from about 1 unit/mg to about 250 units/mg. In embodiments, the compositions disclosed herein comprise from about 0.5 units/mg to about 100 units/mg superoxide dismutase and a soluble fiber. In embodiments, the compositions comprise from about 1 units/mg to about 50 units/mg superoxide dismutase. In embodiments, the compositions comprise from about 5 units/mg to about 25 units/mg superoxide dismutase. In embodiments, the compositions comprise from about 10 units/mg to about 15 units/mg superoxide dismutase. In embodiments, the compositions comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 units/mg superoxide dismutase. In embodiments, the compositions comprise about 14 units/mg superoxide dismutase.

The superoxide dismutase used in the compositions disclosed herein can be obtained from any source of the enzyme. In embodiments, the superoxide dismutase is extracted from melon, bovine liver, heterotrophic bacteria or marine phytoplankton. The superoxide dismutase can also be any type of the enzyme. In embodiments, the superoxide dismutase is a copper/zinc superoxide dismutase, an iron/manganese superoxide dismutase or a nickel superoxide dismutase.

In embodiments, the superoxide dismutase is extracted from a plant. In embodiments, the plant is a fruit, a grain or a tuber. In embodiments, the plant is a fruit selected from melon, citrus fruit, peach, pear, apple or banana. In embodiments, the plant is a grain selected from wheat, barley, rye, millet, oat, spelt, bulger, sorghum and farro. In embodiments, the plant is a tuber selected from horseradish, potato, yam, sweet potato, cassava or dahlia.

In embodiments, the superoxide dismutase is extracted from an animal. In embodiments, the animal is a cow, pig, sheep or goat.

In embodiments, the superoxide dismutase is extracted from a microorganism. In embodiments, the microorganism is phytoplankton or bacteria. In embodiments, the microorganism is a heterotrophic bacteria, e.g., a bacteria that takes the sugars it needs for energy production from their environment.

The ratio of superoxide dismutase to soluble fiber can be adjusted as needed by varying the amount of either or both components of the composition. In embodiments, the ratio of superoxide dismutase to soluble fiber in the composition is from about 1:100 to about 1:1000 by weight. In embodiments, the ratio of superoxide dismutase to soluble fiber in the composition is from about 1:200 to about 1:800 by weight. In embodiments, the ratio of superoxide dismutase to soluble fiber in the composition is from about 1:300 to about 1:700 by weight. In embodiments, the ratio of superoxide dismutase to soluble fiber in the composition is from about 1:500 to about 1:700 by weight. In embodiments, the ratio of superoxide dismutase to soluble fiber in the composition is from about 1:650 to 1:675 by weight.

In embodiments of the compositions disclosed herein, various types of soluble fibers can be used, including mixtures of two, three, four, five, six or more different types of soluble fibers. In embodiments, the soluble fiber is a water soluble polysaccharide. In embodiments, the soluble fiber is isolated from corn, wheat, barley, rye, beans, apples, pears, peaches, citrus fruits, berries, peas, rice bran or oats. In embodiments, the soluble fiber is selected from soluble corn fiber, inulin, dextrin, Guar gum, oligopolysaccharides, galactopolysaccharides fructo-oligosaccharides, lactulose, digestion-resistant starch, xylo-oligosaccharides and isomelto-oligossacharides. In embodiments, the soluble fiber is soluble corn fiber. In embodiments, the soluble fiber is digestion-resistant maltodextrin. In embodiments, the soluble fiber is Fibersol-2@ as sold by Archer Daniels Midland Company and Matsutani Chemical Industry Co., Ltd. In embodiments, the soluble fiber an alternative type of Fibersol-2@ such as Fibersol-2AG, Fibersol-LQ, Fibersol-2L, Fibersol-DLQ or non-GMO Fibersol.

Powder Compositions

In some embodiments of the compositions disclosed herein, the composition is in the form of a powder. In embodiments where the composition is in the form of a powder, it can be consumed in dry powder form or added to a beverage or food. In embodiments, the powder is mixed into water, a hydration beverage, a protein shake, juice, tea, coffee, milk, kefir, ice cream, yogurt, a smoothie, broth or soup prior to consumption.

In embodiments, the powder composition comprises a high concentration of superoxide dismutase by weight, e.g., greater than 0.1 ppm, greater than 0.5 ppm, greater than 1 ppm, greater than 2 ppm, greater than 5 ppm, greater than 10 ppm, greater than 20 ppm, greater than 50 ppm, greater than 100 ppm, greater than 200 ppm, greater than 300 ppm, greater than 400 ppm or greater than 500 ppm. In embodiments, the powder composition comprises from about 0.1 ppm to about 10 ppm superoxide dismutase by weight. In embodiments, the powder composition comprises from about 0.5 ppm to about 5 ppm superoxide dismutase by weight. In embodiments, the powder composition comprises from about 0.7 ppm to about 2 ppm superoxide dismutase by weight. In embodiments, the powder composition comprises from about 0.8 ppm to about 1.2 ppm superoxide dismutase by weight. In embodiments, the powder composition comprises about 0.1, 0.25, 0.5, 0.75, 1.0, 1.1, 1.2, 1.25, 1.3, 1.4, 1.5, 1.6, 1.7, 1.75, 1.8, 1.9, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, or 10.0 ppm superoxide dismutase by weight.

In embodiments, the powder composition comprises from about 1% to about 90% soluble fiber by weight. In embodiments, the powder composition comprises from about 1% to about 50% soluble fiber by weight. In embodiments, the powder composition comprises from about 5% to about 25% soluble fiber by weight. In embodiments, the powder composition comprises from about 10% to about 20% soluble fiber by weight. In embodiments, the powder composition comprises from about 12% to about 14% soluble fiber by weight. In embodiments, the power composition comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% soluble fiber by weight.

Liquid or Gel Compositions

In embodiments of the compositions disclosed herein, the composition is in the form of a gel. In embodiments of the compositions disclosed herein, the composition is in the form of a liquid. In embodiments where the composition is in the form of a gel or liquid, it can be consumed in directly in that form. In other embodiments, the gel or liquid can be added to a beverage or food. In embodiments, the powder is mixed into water, a hydration beverage, a protein shake, juice, tea, coffee, milk, kefir, ice cream, yogurt, a smoothie, broth or soup prior to consumption.

In embodiments, the gel or liquid composition comprises from about 0.005 mg/mL to about 5.0 mg/mL superoxide dismutase. In embodiments, the gel or liquid composition comprises from about 0.01 mg/mL to about 2.5 mg/mL superoxide dismutase. In embodiments, the gel or liquid composition comprises from about 0.05 mg/mL to about 1.0 mg/mL superoxide dismutase. In embodiments, the gel or liquid composition comprises from about 0.1 mg/mL to about 0.5 mg/mL superoxide dismutase. In embodiments, the gel or liquid composition comprises about 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 mg/mL superoxide dismutase.

In embodiments, the gel or liquid composition comprises from about 50 mg/mL to about 1000 mg/mL soluble fiber. In embodiments, the gel or liquid composition comprises from about 70 mg/mL to about 500 mg/mL soluble fiber. In embodiments, the gel or liquid composition comprises from about 90 mg/mL to about 250 mg/mL soluble fiber. In embodiments, the gel or liquid composition comprises from about 100 mg/mL to about 200 mg/mL soluble fiber. In embodiments, the gel or liquid composition comprises about 50, 75, 100, 110, 120, 125, 130, 133, 135, 140, 150, 160, 170, 175, 180, 190, 200, 225, 250, 275, 300, 325, 350, 375, 400, 425, 450, 475 or 500 mg/mL soluble fiber.

Fruit Juices

In embodiments of the compositions disclosed herein, the composition comprising superoxide dismutase and soluble fiber also comprises a fruit juice. The fruit juice can provide additional antioxidants, soluble fiber, insoluble fiber, vitamins and nutrients to the composition.

In embodiments, the fruit juice is pomegranate juice, red grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice, prune juice or combinations thereof. In embodiments, the composition comprises two, three four, five or six types of juice selected from: pomegranate juice, red grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice and prune juice.

In embodiments, the fruit juice can be concentrated, e.g., having some of the water in the original juice removed. In embodiments, the fruit juice is concentrated pomegranate juice, red grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice, prune juice or combinations thereof. In embodiments, the composition comprises two, three four, five or six types of concentrated juice selected from: concentrated pomegranate juice, concentrated red grape juice, concentrated blueberry juice, concentrated dark sweet cherry juice, concentrated sour cherry juice, concentrated goji berry juice, concentrated acai berry juice, concentrated blackberry juice, concentrated raspberry juice, concentrated strawberry juice, concentrated gooseberry juice, concentrated cranberry juice, concentrated orange juice, concentrated grapefruit juice, concentrated watermelon juice, concentrated beet juice, concentrated apple juice, concentrated lemon juice, concentrated lime juice, concentrated lychee juice, concentrated pineapple juice, concentrated prune juice. In embodiments, the concentrated fruit juice has about 60% to about 97% of the water of the juice removed. In embodiments, the concentrated fruit juice has about 85% to about 95% of the water of the juice removed. In embodiments, the concentrated fruit juice has about 60%, 65%, 70%, 75%, 80%, 85%, 90%, 95%, 96%, 97%, 98% or 99% of the water of the fruit juice removed. Water can be removed from the fruit juices using any method known in the art for concentrating fruit juices.

In embodiments, the composition comprises from about 5 mg/mL to about 200 mg/mL of the concentrated fruit juice. In embodiments, the composition comprises from about 75 mg/mL to about 150 mg/mL concentrated pomegranate juice. In embodiments, the composition comprises from about 75 mg/mL to about 150 mg/mL concentrated red grape juice. In embodiments, the composition comprises from about 25 mg/mL to about 100 mg/mL concentrated blueberry juice. In embodiments, the composition comprises from about 20 mg/mL to about 80 mg/mL concentrated dark sweet cherry juice. In embodiments, the composition comprises from about 20 mg/mL to about 80 mg/mL concentrated sour cherry juice. In embodiments, the composition comprises from about 2 mg/mL to about 20 mg/mL concentrated goji berry juice. In embodiments, the composition comprises from about 2 mg/mL to about 20 mg/mL concentrated acai berry juice.

Other Additional Components

In embodiments of the compositions disclosed herein, the composition comprising superoxide dismutase and soluble fiber also comprises aloe vera. The aloe vera can provide additional antioxidants, soluble fiber, insoluble fiber, vitamins and nutrients to the composition.

In some embodiments, the aloe vera is concentrated aloe vera. In embodiments, the aloe vera can be concentrated, e.g., having some of the water removed from the aloe vera that is extracted from the aloe vera plant. In embodiments, the concentrated aloe vera has about 60% to about 97% of the water of the aloe vera removed. In embodiments, the concentrated aloe vera has about 60%, 65%, 70%, 75%, 80%, 85%, 90%, 95%, 96%, 97%, 98% or 99% of the water of the aloe vera removed. In embodiments, the composition comprises from about 2 mg/mL to about 20 mg/mL concentrated aloe vera.

In embodiments of the compositions disclosed herein, the composition comprising superoxide dismutase and soluble fiber also comprises green tea. The green tea can provide additional antioxidants, vitamins and nutrients to the composition.

In embodiments, the green tea is concentrated green tea. In embodiments, the concentrated green tea is a green tea extract made from green tea leaves or green tea powder. In embodiments, the green tea is added to the composition in powder form. In embodiments, the composition comprises from about 2 mg/mL to about 20 mg/mL concentrated green tea.

In embodiments of the compositions disclosed herein, the composition comprising superoxide dismutase and soluble fiber also comprises resveratrol. The resveratrol can provide additional antioxidants to the composition. In some embodiments, the composition comprises from about 0.5 mg/mL to about 6 mg/mL resveratrol.

Excipients/Formulations

In embodiments, the compositions disclosed herein can be combined with one or more excipient. In embodiments, the excipient is a gelling agent, a thickening agent, a carrier, a buffer or a filler. In embodiments, the compositions disclosed herein can be formulated into beverages or foodstuffs. In embodiments, the compositions are formulated into juice, a hydration beverage (e.g. a sports drink), a protein shake, tea, coffee, milk, kefir, ice cream, yogurt, a smoothie, broth or soup.

In embodiments, the compositions comprise the thickener/gelling agent carboxymethyl cellulose. In embodiments, composition is a gel comprising superoxide dismutase, soluble fiber and carboxymethyl cellulose. In embodiments, the composition comprises from about 0.5 to about 5.0 mg/mL carboxymethyl cellulose.

In embodiments, the compositions comprise the thickener/gelling agent xanthan gum. In embodiments, composition is a gel comprising superoxide dismutase, soluble fiber and xanthan gum. In embodiments, the composition comprises from about 0.5 to about 5.0 mg/mL xanthan gum.

In embodiments, the composition comprises: a) from about 0.5 units/mg to about 100 units/mg superoxide dismutase; b) a soluble fiber; and c) at least two fruit juices selected from pomegranate juice, red grape juice, blueberry juice, dark sweet cherry juice, sour cherry juice, goji berry juice and acai berry juice. In embodiments, the composition comprises at least three fruit juices. In embodiments, the composition comprises at least four fruit juices. In embodiments, the composition comprises at least five fruit juices. In embodiments, the composition comprises at least six fruit juices. In embodiments, the composition comprises pomegranate juice, red grape juice, blueberry juice, dark sweet cherry juice, sour cherry juice, goji berry juice and acai berry juice. In embodiments of the composition, the fruit juices are concentrated fruit juices. In embodiments of the composition, the soluble fiber is soluble corn fiber. In embodiments, the soluble corn fiber is digestion-resistant maltodextrin.

In embodiments, the composition comprises: a) superoxide dismutase; b) a soluble corn fiber; c) at least two fruit juices selected from pomegranate juice, red grape juice, blueberry juice, dark sweet cherry juice, sour cherry juice, goji berry juice and acai berry juice; d) aloe vera; e) green tea; and f) resveratrol. In embodiments, the composition comprises at least three fruit juices. In some embodiments, the composition comprises at least four fruit juices. In embodiments, the composition comprises at least five fruit juices. In embodiments, the composition comprises at least six fruit juices. In embodiments, the composition comprises pomegranate juice, red grape juice, blueberry juice, dark sweet cherry juice, sour cherry juice, goji berry juice and acai berry juice. In embodiments of the composition, the fruit juices are concentrated fruit juices. In embodiments of the composition, the soluble corn fiber is digestion-resistant maltodextrin. In embodiments, the composition also comprises carboxymethylcellulose. In embodiments, the composition also comprises xanthan gum.

In embodiments, the composition comprises: a) from about 30 units to about 1000 units superoxide dismutase; b) from about 50 mg/mL to about 200 mg/mL of a soluble corn fiber; c) from about 5 mg/mL to about 200 mg/mL each of at least two concentrated fruit juices selected from pomegranate juice, red grape juice, blueberry juice, dark sweet cherry juice, sour cherry juice, goji berry juice and acai berry juice; d) from about 2 mg/mL to about 20 mg/mL concentrated aloe vera; e) from about 2 mg/mL to about 20 mg/mL concentrated green tea; and f) from about 0.5 mg/mL to about 6 mg/mL resveratrol. In embodiments of the composition, the soluble corn fiber is digestion-resistant maltodextrin. In embodiments, the composition also comprises about 0.5 to about 5.0 mg/mL carboxymethyl cellulose. In embodiments, the composition also comprises from about 0.5 to about 5.0 mg/mL xanthan gum.

In some embodiments, the present invention provides a nutritional liquid formulation containing soluble fiber and a plurality of antioxidants.

In some embodiments, the formulation includes soluble corn fiber. The corn fiber can constitute about 1 to about 5 weight percent of the total formulation. The corn fiber can be in the form of a dry powder.

In some embodiments, the soluble fiber can be a corn-based digestion resistant maltodextrin (Fibersol-2) pre-biotic fiber. Pre-biotic is selectively fermented ingredient that allows specific changes, both in composition and/or activity of the gut microbiota that confers health benefits.

In some embodiments, the antioxidants of the formulation include various polyphenols. The polyphenols can constitute about 1 to about 3 weight percent of the total formulation. In some embodiments, the antioxidants of the formulation include superoxide dismutases (SOD).

In some embodiments, the present disclosure provides a nutritional supplement formulation containing soluble corn fiber, concord red grape (*Vitis labrusca*) juice concentrate, pomegranate (*Punica granatum*) juice concentrate, blueberry (*Vaccinium corymbosum*) juice concentrate, dark sweet cherry (*Prunus avium*) juice concentrate, sour cherry (*Prunus cerasus*) juice concentrate, Goji berry (*Lycium barbarum*) puree, Acai (*Euterpe oleraceae*) berry juice concentrate, Aloe vera juice concentrate (*Aloe barbadensis* Mill), Green tea extract (*Camellia sinensis*), Resveratrol, Melon fruit juice concentrate (*Cucumis melo* L, and Extramel-SOD).

The soluble fiber and the antioxidants formulations of the present disclosure provide synergistic effects in that the soluble pre-biotic fiber acts as a fertilizer for the bacteria in the colon, while the polyphenols are absorbed in a substantial part in the colon and subject to extensive catabolism by colonic microbiota. The presence of the pre-biotic fiber enhances the action of the colonic microbiota, thereby leading to more effective absorption of the polyphenols in the colon. A large majority of polyphenols from an antioxidant supplement end up in the large intestine where they undergo microbial metabolism into their active metabolites where they can exert an antioxidant effect. The soluble fiber modulates the gut microbes and maximizes polyphenol metabolism, producing many antioxidant, anti-inflammatory, and anti-infection effects.

In some embodiments, the composition comprises the ingredients shown in Table 1 at the amounts indicated.

TABLE 1

Revivify Anti - Oxidant Composition
17.88 g/30 ml

| SI. # | Propreatary Blend 17.88 g | QTY/mg | |
|---|---|---|---|
| 1 | Soluble corn fiber (Fibersol-2) | 4000 | |
| 2 | Pomegranate Juice Concentrate | 4000 | |
| 3 | Concord Grape Juice Concentrate | 4000 | |
| 4 | Blueberry Juice Concentrate | 2000 | |
| 5 | Dark Sweet Cherry Juice Concentrate | 1450 | |
| 6 | Sour Cherry Juice Concentrate | 1450 | |
| 7 | Goji Pulp | 294 | |
| 8 | Acai Concentrate Juice | 200 | |
| 9 | Alobira Juice | 200 | |
| 10 | Green Tea | 200 | |
| 11 | Resveratrol | 80 | |
| 12 | Extramel SOD (14000 unit/g) | 6 | 17880 |

TABLE 1-continued

Revivify Anti - Oxidant Composition
17.88 g/30 ml

| SI. # | Propreatary Blend 17.88 g | QTY/mg |
|---|---|---|
| 13 | CMC | 60.5 |
| 14 | Xanthan | 60.5 |
| 15 | QS Water (30 ml) | |

Reactive Oxygen Species and Oxygen Radical Absorbance Capacity

In embodiments, the compositions disclosed herein are useful in reducing the level of reactive oxygen species (ROS) in cells. In embodiments, the reactive oxygen species reduced in levels include one or more of a peroxide, superoxide, hydroxyl radical, singlet oxygen and alpha-oxygen species. In embodiments, the reactive oxygen species reduced in levels include one or more of a peroxyl radical, hydroxyl radical, peroxynitrite, super oxide anion, single oxygen or hypochlorite species.

The disclosure provides the discovery that compositions comprising superoxide dismutase in combination with soluble fiber results in greatly increased oxygen radical absorbance capacity (ORAC). The addition of soluble fiber to a composition comprising superoxide dismutase provides a synergistic effect for increasing the oxygen radical absorbance capacity, i.e., the ORAC value of the combination is much greater than the additive value of the superoxide dismutase and soluble fibers not in combination.

In embodiments, the ability of a composition disclosed herein to reduce the level of reactive oxygen species in cells is measured by measuring the oxygen radical absorbance capacity (ORAC) of the composition. Examples of ORAC assays are known in the art. See, for example "Chapter 2—Methods for Measuring Oxidative Stress in the Laboratory" by A. Dasgupta et al. at pp. 19-40 of *Antioxidants in Food, Vitamins and Supplements* (2014, Elsevier), which is hereby incorporated by reference herein.

In general, the ORAC assay measures the antioxidant capacity of a substance. The ORAC assay measures a fluorescent signal from a probe that is quenched in the presence of reactive oxygen species. A reactive oxygen species inducer is introduced to the assay system. The inducer triggers the release of a specific reactive oxygen species, which would degrade the probe and cause an emission wavelength or intensity change from the probe. The antioxidant materials present in the assay absorbs the reactive oxygen species and preserves the probe from degradation. The degree of probe preservation thus indicates the antioxidant capacity of the material.

In embodiments, the fluorescent probe used in the ORAC assay is beta-phycoerythrin or fluorescein. In embodiments, the ORAC capacity of an antioxidant is measured compared to a standard. In embodiments, the standard is the known antioxidant Trolox® (6-hydroxy-2,5,7,8-tetramethylchromane-2-carboxylic acid), which is a vitamin E analogue. In embodiments where Trolox® is used as the standard, the results can be expressed as the "Total Antioxidant Capacity" (TAC) for the tested molecule and expressed as micromole (µmol) Trolox® equivalency (TE) per gram of the antioxidant molecule tested.

In embodiments, the ORAC assay measures one or more of the reactive oxygen species peroxyl radicals, hydroxyl radicals, peroxynitrie, superoxide dismutase, singlet oxygen, and hypochlorite. In embodiments, the ORAC assay is the ORAC 6.0 assay performed by Brunswick Laboratories in Southborough, Mass., USA. The ORAC 6.0 assay tests for antioxidant capacity against peroxyl radicals, hydroxyl radicals, peroxynitrie, superoxide dismutase, singlet oxygen, and hypochlorite.

In embodiments of any of the compositions disclosed herein, the composition has a total ORAC of greater than 1000 mol/g of the composition. In embodiments of any of the compositions disclosed herein, the composition has an ORAC of greater than 1500 µmol/g of the composition. In embodiments of any of the compositions disclosed herein, the composition has a total ORAC of greater than 700, 800, 900, 1000, 1100, 120, 1300, 1400, 1500, 1600, 1700, 1800, 1900 or 2000 mol/g of the composition. As used herein "total ORAC" refers to the sum of the ORAC value for each reactive oxygen species. For example, in embodiments where the ORAC 6.0 assay is used, the total ORAC is the sum of the ORAC values for each of peroxyl radicals, hydroxyl radicals, peroxynitrie, superoxide dismutase, singlet oxygen, and hypochlorite. In embodiments, the total ORAC value is divided by the weight of the composition in grams to give a value of µmol/g.

In embodiments of any of the compositions disclosed herein, an ORAC value for the composition is at least 1.5 fold higher than the sum of individual ORAC values for each component of the composition. In embodiments of any of the compositions disclosed herein, an ORAC value for the composition is at least 1.6 fold higher than the sum of individual ORAC values for each component of the composition. In embodiments of any of the compositions disclosed herein, an ORAC value for the composition is at least 1.1, 1.2, 1.3, 1.4, 1.5, 1.6, 1.7, 1.8, 1.9, 2.0, 2.1, 2.2, 2.3, 2.4 or 2.5 fold higher than the sum of individual ORAC values for each component of the composition.

Viscosity

In embodiments, the compositions disclosed herein have viscosity properties that stabilize the composition. In embodiments, the composition is a high viscosity gel that is shelf stable, retains its flavor over time and allows for minimal oxygen permeation into the composition. In embodiments, the composition is thixotropic, having a high viscosity when stored and a lower viscosity when agitated, for example, by shaking or administration. In embodiments, the composition is thixotropic and is a high viscosity gel having good stability properties when stored and has a lower viscosity when administered, allowing for ease of administration and ingestion and favorable distribution in the gastrointestinal tract and good absorption. In embodiments, the composition has a viscosity of about 23 poise or greater at a shear rate of 1/sec. In embodiments, the composition has a viscosity of about 5 poise or less at a shear rate of 10/sec. In embodiments, the composition has a viscosity of about 1 poise or less at a shear rate of 100/sec. In embodiments, the composition has a viscosity of about 23 poise or greater at a shear rate of 1/sec, a viscosity of about 5 poise or less at a shear rate of 10/sec and a viscosity of about 1 poise or less at a shear rate of 100/sec.

Methods

The present disclosure is also directed to a method of reducing the number of free oxygen radicals in a mammal, comprising administering to the mammal any of the compositions disclosed herein. In embodiments, the free oxygen radicals to be reduced in number are selected from peroxyl radicals, hydroxyl radicals, peroxynitrite, superoxide anion, singlet oxygen, hypochlorite and combinations thereof. In embodiments, the method may reduce two, three, four five or six types of free oxygen radicals. In embodiments, the free oxygen radicals to be reduced in number are selected from peroxyl radicals, hydroxyl radicals, peroxynitrite, superoxide anion singlet oxygen and hypochlorite in the mammal.

In some embodiments, the synergistic effect observed with the superoxide dismutase/soluble fiber combinations provide for increased oxygen radical absorbance capacity (ORAC) that is beneficial reducing inflammation. The present disclosure is further directed to a method of reducing inflammation in a mammal, comprising administering to the mammal any of the compositions disclosed herein. The present disclosure is further directed to methods of treating in a mammal any disease or disorder associated with increased levels of reactive oxygen species, comprising administering to the mammal any of the compositions disclosed herein. In embodiments, the disease or disorder can be a bacterial infection; a viral infection; radiation sickness; a demyelinating disease such as multiple sclerosis or a neuropathy; a joint disorder such as arthritis, rheumatoid arthritis, or psoriatic arthritis; a skin disorder such as psoriasis, rosacea, acne vulgaris, dermatitis, or hives; a neurodegenerative disorder such as multiple sclerosis, Parkinson's disease, amyotrophic lateral sclerosis, Alzheimer's disease, or Huntington's disease; a neuromuscular disease such as Muscular Dystrophy, Myasthenia Gravis; tremors; disorders of the gut such as digestive inflammation, inflammatory bowel disease, Crohn's disease, colitis, diarrhea, leaky gut syndrome, diverticulitis, or Celiac disease; asthma; inflammatory diseases such as autoimmune disease, diabetes, gout, chronic prostatitis, glomerulonephritis, hidradenitis suppurativa, interstitial cystitis, lichen planus, Mast Cell Activation Syndrome, mastocytosis, otitis, pelvic inflammatory disease; reperfusion injury; chronic fatigue syndrome; rheumatic fever; rhinitis; sarcoidosis; transplant rejection; and vasculitis.

In some embodiments, the synergistic effect observed with the superoxide dismutase/soluble fiber combinations provide for increased oxygen radical absorbance capacity (ORAC) that is beneficial in the prevention and treatment of viral infections. In embodiments, the compositions disclosed herein can be used in methods for preventing viral infections, including infections of influenza A, influenza B, influenza C, influenza D, coronaviruses including SARS (severe acute respiratory syndrome), SARS-CoV-2 (causing COVID-19), MERS (Middle East respiratory syndrome), HIV, Ebola, rhinovirus and respiratory syncytial virus. In embodiments, the compositions disclosed herein can be used in methods for treating viral infections, including infections of influenza A, influenza B, influenza C, influenza D, coronaviruses including SARS (severe acute respiratory syndrome), SARS-CoV-2 (causing COVID-19), MERS (Middle East respiratory syndrome), HIV, Ebola, rhinovirus and respiratory syncytial virus.

In some embodiments, the synergistic effect observed with the superoxide dismutase/soluble fiber combinations provide for increased oxygen radical absorbance capacity (ORAC) that is beneficial for supplementing the diet of a subject undergoing cancer treatment. In embodiments, the compositions disclosed herein can be used in methods for supplementing the diet of a mammal that is undergoing cancer treatment, has been exposed to radiation or is suffering from malnutrition.

In embodiments of any of the methods disclosed herein, the composition is administered to the mammal once a day. In embodiments of any of the methods disclosed herein, the composition is administered to the mammal twice a day. In embodiments of any of the methods disclosed herein, the composition is administered to the mammal three, four, five, six, seven, eight nine, ten times or more a day.

In embodiments of any of the methods disclosed herein, the mammal is a human. In embodiments, of any of the methods disclosed herein the mammal is a primate (e.g., monkey, ape, gorilla, macaque), a household animal (e.g., dog, cat, rabbit, hamster, Guinea pig, mouse, rat) or an agricultural animal (e.g., cow, sheep, horse, goat, pig).

EXAMPLES

Example 1: Example Formulation

An example formulation was prepared having the ingredient and concentrations shown in Table 2:

TABLE 2

| SI. # | Ingredient | QTY in mg |
|---|---|---|
| 1 | Soluble corn fiber (Fibersol-2) | 4000 |
| 2 | Pomegranate Juice Concentrate | 4000 |
| 3 | Concord Grape Juice Concentrate | 4000 |
| 4 | Blueberry Juice Concentrate | 2000 |
| 5 | Dark Sweet Cherry Juice Concentrate | 1450 |
| 6 | Sour Cherry Juice Concentrate | 1450 |
| 7 | Goji Pulp | 294 |

TABLE 2-continued

| SI. # | Ingredient | QTY in mg |
|---|---|---|
| 8 | Acai Concentrate Juice | 200 |
| 9 | Aloe vera juice | 200 |
| 10 | Green Tea | 200 |
| 11 | Resveratrol | 80 |
| 12 | Extramel SOD (14000 unit/g) | 6 |
| 13 | CMC | 60.5 |
| 14 | Xanthan | 60.5 |
| 15 | OS Water (30 ml) | |

Ingredients 1-12 were combined into a homogeneous blend using a stainless steel mixing tank. Prior to mixing, the ingredients are weighed according to batch size. The juice concentrate is first completely mixed in a separate tank, then solid ingredients are premixed with water in a separate mixer and the two mixtures are combined in the main mixing tank. Sufficient water is added to volume and the product is mixed properly. The final product is pasteurized prior to packaging in a pouch. The formulation is a gel that is dark red in color.

Example 2: ORAC Testing of Example Formulation

Tests were performed to determine the ORAC value of different components of the formulation of Example 1 compared to the formulation as a whole. Individual component samples were prepared using the amount by weight of the sample in the total formulation: Sample A: 4 g soluble corn fiber (Fibersol-2®); Sample B: 13.8749 g fruit juice concentrate mixture; and Sample C: 0.006 g superoxide dismutase isolated from melon. Sample D was the finished product formulation which had a weight of 31.1 g. Samples were sent to Brunswick Laboratories (Southborough, Mass., USA) for testing using the ORAC 6.0 assay as described above and at brunswicklabs.com/capabilities/bioanalytical-services/orac-family/orac6/. Results of the assay are provided in Table 3, with "Test Results" expressed in μmol Trilox equivalents per gram of sample tested. The column "Conversion" provides a conversion of the ORAC value normalized for the amount of sample.

TABLE 3

| | ORAC Value μmole TE/gram *TE = Trolox equivalency | | | | | | | | |
|---|---|---|---|---|---|---|---|---|---|
| | A. (Soluble Corn Fiber, Fibersol-2) 4 g | | B. (Fruit Juice Concentrate) 13.8749 g | | C. (SOD - Melon Source) 0.006 g | | A + B + C Final Value | D. Finished Product (30 ml W 31.1 g) | |
| | Test Results | Conversion | Test Results | Conversion | Test Results | Conversion | Converted Result | Test Results | Conversion |
| Peroxyl radicals | 1.50 | 6 | 128.04 | 1776.52 | ND | ND | 1782.52 | 112.27 | 3,491.56 |
| Hydroxyl radicals | ND | ND | 648.11 | 8992.46 | ND | ND | 8992.46 | 416.46 | 12,951.91 |
| Peroxy nitrite | 0.24 | 0.96 | 34.46 | 478.13 | ND | ND | 479.09 | 22.76 | 707.84 |
| Super oxide anion | ND | ND | 176.57 | 2449.89 | ND | ND | 2449.89 | 134.2 | 4,173.62 |
| Singlet oxygen | ND | ND | 182.36 | 2516.36 | ND | ND | 2516.36 | 109.20 | 3,396.12 |
| Hypochlorite | ND | ND | 926.85 | 12859.96 | 16.83 | 0.10098 | 12860.07 | 749.22 | 23,300.74 |
| Total | 1.84 | 6.96 | 2,096.39 | 29,087.20 | 16.83 | 0.10098 | 29,094.26 | 1,544.61 | 48,021.79 |

As can be seen in Table 3, the finished product Sample D shows an unexpected and significantly higher ORAC value (48,021.79) compared to the total of individual component Samples A-C (29,094.26). Thus, the ORAC testing suggests a synergistic effect between to components of the formulation of Example 1 when these components are combined. Without wishing to be bound by theory, one potential contribution to this synergistic effect is a possible stabilizing effect that the other ingredients have on the superoxide dismutase enzyme, allowing the superoxide dismutase to more effectively neutralize reactive oxygen species.

Example 3: Viscosity Testing of Example Formulation

The viscosity of the formulation of Example 1 was tested under various amounts of shear stress. A dynamic viscometer was used to test 5 mL of the formulation gel at a temperature of 25° C. The viscosity (in poise) was tested for two separate samples of the formulation gel under increasing shear stress and shear rate over time as shown in Tables 4 and 5. The normal stress at each time point is also shown.

TABLE 4 viscosity of gel formulation sample 1 (5 mL) under increasing shear stress.

| shear stress dyne/cm^2 | shear rate 1/sec | viscosity poise | time sec | temperature ° C. | normal stress dyne/cm^2 |
|---|---|---|---|---|---|
| 9.156 | 0.09999 | 91.56 | 60.5 | 25 | −5804 |
| 12.02 | 0.1585 | 75.81 | 125.53 | 25 | −6041 |
| 14.58 | 0.2512 | 58.05 | 190.5 | 25 | −6266 |
| 17.35 | 0.3981 | 43.57 | 255.53 | 25 | −6536 |
| 20.42 | 0.631 | 32.36 | 320.52 | 25 | −6686 |
| 23.85 | 1 | 23.85 | 385.5 | 25 | −6706 |
| 27.66 | 1.585 | 17.45 | 450.55 | 25 | −6558 |
| 32.03 | 2.512 | 12.75 | 515.58 | 25 | −6370 |
| 37.1 | 3.981 | 9.32 | 580.52 | 25 | −6290 |
| 43.19 | 6.31 | 6.845 | 645.53 | 25 | −6199 |
| 50.68 | 10 | 5.068 | 710.53 | 25 | −6252 |
| 60.15 | 15.85 | 3.795 | 775.53 | 25 | −6420 |
| 71.93 | 25.12 | 2.863 | 840.52 | 25 | −6842 |
| 87.02 | 39.81 | 2.186 | 905.53 | 25 | −7154 |
| 106.8 | 63.1 | 1.693 | 970.52 | 25 | −7429 |
| 133.1 | 100 | 1.331 | 1035.5 | 25 | −7560 |
| 167.9 | 158.5 | 1.059 | 1100.5 | 25 | −7728 |
| 213.8 | 251.2 | 0.851 | 1165.5 | 25 | −7875 |
| 280.2 | 398.1 | 0.7039 | 1230.5 | 25 | −8092 |
| 374.8 | 631 | 0.5941 | 1295.5 | 25 | −8536 |
| 509 | 1000 | 0.509 | 1360.5 | 25 | −9372 |

TABLE 5 viscosity of gel formulation sample 2 (5 mL) under increasing shear stress.

| shear stress dyne/cm^2 | shear rate 1/sec | viscosity poise | time sec | temperature ° C. | normal stress dyne/cm^2 |
|---|---|---|---|---|---|
| 9.444 | 0.1 | 94.42 | 60.984 | 25 | −2232 |
| 13.28 | 0.1585 | 83.8 | 125.97 | 25 | −2797 |
| 16.31 | 0.2512 | 64.92 | 190.92 | 25 | −3238 |
| 18.74 | 0.3981 | 47.07 | 255.95 | 25 | −3653 |
| 21.27 | 0.631 | 33.71 | 320.95 | 25 | −4024 |
| 24.37 | 1 | 24.37 | 385.92 | 25 | −4395 |
| 28.04 | 1.585 | 17.69 | 450.94 | 25 | −4734 |
| 32.16 | 2.512 | 12.8 | 515.92 | 25 | −5045 |
| 36.82 | 3.981 | 9.25 | 580.94 | 25 | −5344 |
| 42.17 | 6.31 | 6.684 | 645.98 | 25 | −5693 |
| 48.37 | 10 | 4.837 | 710.92 | 25 | −5939 |
| 55.84 | 15.85 | 3.523 | 775.95 | 25 | −6198 |
| 65.62 | 25.12 | 2.613 | 840.98 | 25 | −6154 |
| 78.27 | 39.81 | 1.966 | 905.97 | 25 | −6107 |
| 94.9 | 63.1 | 1.504 | 970.94 | 25 | −6040 |
| 117 | 100 | 1.17 | 1036 | 25 | −5768 |
| 147.5 | 158.5 | 0.9309 | 1101 | 25 | −5671 |
| 188.4 | 251.2 | 0.7502 | 1166 | 25 | −5826 |
| 249.1 | 398.1 | 0.6256 | 1231 | 25 | −6237 |
| 330.8 | 631 | 0.5244 | 1295.9 | 25 | −6803 |
| 445.3 | 1000 | 0.4453 | 1361 | 25 | −7822 |

Figure 1:
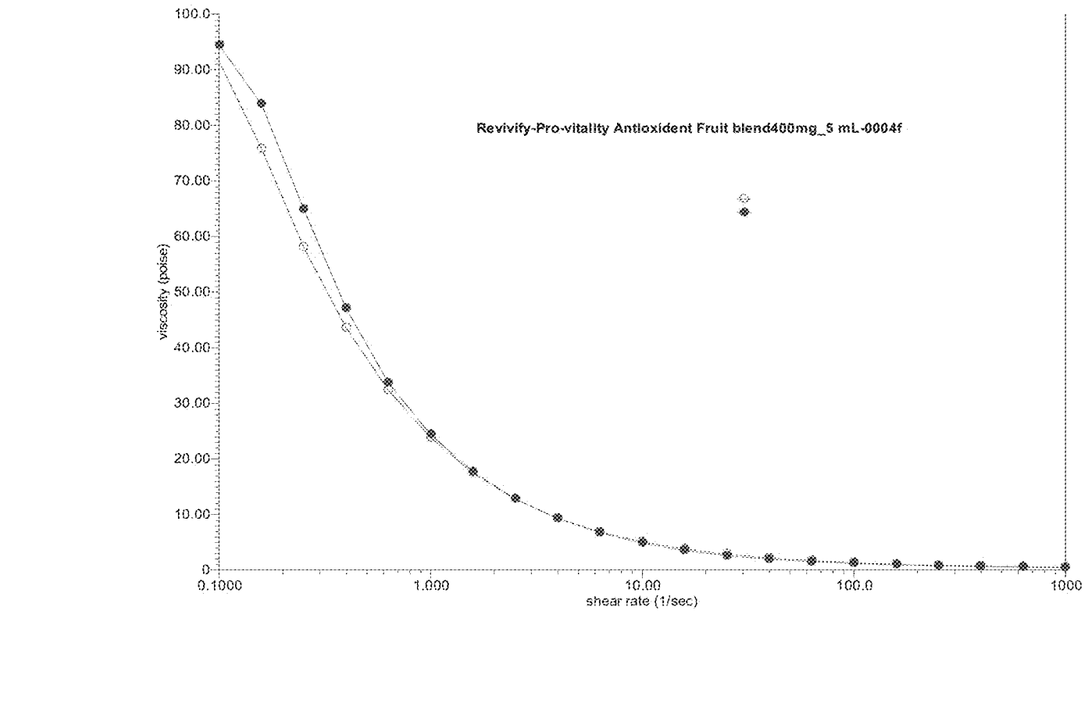
FIG. 1 is a plot of viscosity (poise) vs. shear rate (1/sec) for two 5 mL samples of the gel formulation of Example 1 as tested in Example 3—open circles: sample 1; closed circles: sample 2.

The results provided in Tables 4 and 5 are plotted in FIG. 1. As can be seen in Tables 4 and 5 and FIG. 1, the gel formulation is surprisingly thixotropic as it becomes less viscous upon application of shear stress. This thixotropic property can provide several advantages to the gel formulation. At rest, the gel formulation is a high viscosity gel that help the product to maintain its physical composition, retain its flavor and minimize oxygen permeation. During administration, agitation of the gel formulation causes it to become less viscous and this resulting increase in fluidity eases oral administration while also favoring distribution of the formulation in the gastrointestinal tract, thus facilitating absorption.

Example 4: Improved Recovery in COVID-19 Patients

It was theorized that the superoxide dismutase and soluble fiber compositions described herein help to strengthen the immune system, allowing a subject taking the composition to be more resistant to catching a viral or bacterial infection and also better able to recover more quickly from a viral or bacterial infection. The gel formulation of Example 1 was thus given to several patients that had tested positive for COVID-19, the disease caused by the Sars-CoV-2 virus. Current indications from medical professional and researchers are that it can take up to two weeks to recover from COVID-19. Every patient given the gel formulation, regardless of age or gender, was able to recover more quickly than expected.

Patient 1, a male between the ages of 41-50, tested positive for COVID-19 and was suffering from a fever, cough and loss of taste. He began to take the gel formulation twice daily five days after his positive test. Within three to four days of beginning to take the gel formulation, Patient 1 reported feeling much better, with less fatigue and more energy.

Patient 2, a female between the ages of 18-20, tested positive for COVID-19 and was suffering from a fever, cough and headache. She began to take the gel formulation once daily on the day of her positive test. Within three to four days of beginning to take the gel formulation, Patient 2 reported feeling better, and was feeling more energetic and less fatigued.

Patient 3, a male between the ages of 31-40, tested positive for COVID-19 and was suffering from fever, cough and headache while feeling very weak. He began to take the gel formulation once or twice daily four days after his positive test. Within two days of beginning to take the gel formulation, Patient 3 reported feeling better, no longer feeling weak and having more energy.

Patient 4, a female between the ages of 61-70, tested positive for COVID-19 and was hospitalized with symptoms of fever, cough, headache and loss of taste. She began to take the gel formulation once daily five days after her positive test. Within three to four days she was feeling better with more energy and less fatigue.

Patient 5, a male between the ages of 20-30, tested positive for COVID-19 and was suffering from fever, cough and headache. He began to take the gel formulation once daily three days following his positive test. Within two to four days he was feeling better and was feeling energetic and less fatigued.

Example 5: Improvement of Fatigue Related to Diabetes

The patient was a middle-aged female who had been recently diagnosed with diabetes. Even while following a careful diet, the suffered from overwhelming fatigue and had AC levels as high as 10.2%. She began to take the gel formulation of Example 1 and by the end of the first day taking it was starting to feel energetic. After three days of taking the gel formulation, she reported having energy "beyond my wildest dreams."

Example 6: Improvement of Symptoms of Myasthenia Gravis

The patient was a female between the ages of 35-45 who has a rare form of Muscular Dystrophy called Myasthenia Gravis. The disease affected almost her entire muscular system, including her breathing, walking, speaking, swallowing and eye movement. In July 2019 she was hospitalized with her condition and needed to use a wheelchair. She could not walk more than a few feet and struggled to breath. She was put on a regimen of prednisone for her symptoms with a daily dose of 40 mg. She began to take the gel formulation of Example 1 once daily along with a powder superoxide dismutase/soluble fiber formulation as described herein once daily. Three days later she began to feel her symptoms improving and had more energy. After several months of taking this combination of gel formulation and powder formulation, she is now only taking 5 mg of prednisone daily, is able to be active and walk long distances. And she no longer has problems swallowing or speaking and no longer has eye movement issues.

Example 7: Improvement of Symptoms of Multiple Sclerosis

The patient was a female between the ages of 35-45 who has multiple sclerosis. Her symptoms originally began in her legs but then progressed to her right arm. She was frequently in pain, suffered from overwhelming fatigue and had problems sleeping. She began to take the gel formulation of Example 1 and soon thereafter was able to move her right arm with less pain. After taking the product for several months she was feeling much less pain and fatigue and was sleeping better. She was able to reduce the amount of medications she was taking and went from only able to walk about 3,500 steps per day to walking 11,000 steps per day.

Example 8: Improvement of Symptoms of Gout

The patient was a male between the ages of 40-50 who suffers from gout. He originally started taking the gel formulation of Example 1 as a post-workout recovery supplement and noticed that after one month his symptoms were improved. When his gout flared up he took the gel formulation of Example 1 twice daily and his symptoms were under control after two days.

Example 9: Improved Recovery from Viral Symptoms

The patient was a female who was suffering from viral symptoms including difficulty breathing and loss of taste. She was tested for COVID-19 but the result was negative. She took the gel formulation of Example 1 twice daily. After three days she was feeling significantly better and after five days had no viral symptoms.

It will be readily apparent to one of ordinary skill in the relevant arts that other suitable modifications and adaptations to the methods and applications described herein can be made without departing from the scope of any of the embodiments. The above examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A composition comprising:
   a) from about 0.005 mg/mL to about 3.0 mg/mL superoxide dismutase;
   b) from about 70 mg/mL to about 500 mg/mL soluble pre-biotic fiber selected from soluble corn fiber, inulin, Guar gum, polysaccharide fiber, galactopolysaccharides, fructo-oligosaccharides, lactulose, digestion-resistant starch, xylo-oligosaccharides and isomalto-oligossacharides; and
   c) a fruit juice;
   wherein the composition is in the form of a gel.

2. The composition of claim 1, wherein the superoxide dismutase is extracted from melon, bovine liver, heterotrophic bacteria or marine phytoplankton.

3. The composition of claim 1, wherein the superoxide dismutase is a copper/zinc superoxide dismutase, an iron/manganese superoxide dismutase or a nickel superoxide dismutase.

4. The composition of claim 1, wherein the superoxide dismutase is extracted from an animal.

5. The composition of claim 4, wherein the animal is a cow, pig, sheep or goat.

6. The composition of claim 1, wherein the ratio of superoxide dismutase to soluble pre-biotic fiber is from about 1:100 to about 1:1000 by weight.

7. The composition of claim 1, wherein the soluble pre-biotic fiber is a water soluble polysaccharide.

8. The composition of claim 1, wherein the soluble pre-biotic fiber is soluble corn fiber.

9. The composition of claim 8, wherein the soluble corn fiber is digestion-resistant maltodextrin.

10. The composition of claim 1, wherein the fruit juice is pomegranate juice, Concord grape juice, blueberry juice, dark sweet cherry juice, sour cherry juice, goji berry juice, acai berry juice, blackberry juice, raspberry juice, strawberry juice, gooseberry juice, cranberry juice, orange juice, grapefruit juice, watermelon juice, beet juice, apple juice, lemon juice, lime juice, lychee juice, pineapple juice, prune juice or combinations thereof.

11. The composition of claim 10, wherein the fruit juice is a concentrated fruit juice having about 60% to about 97% of the water of the juice removed.

12. The composition of claim 11, wherein the composition comprises from about 5 mg/mL to about 200 mg/mL of the concentrated fruit juice.

13. The composition of claim 1, further comprising aloe vera.

14. The composition of claim 13, wherein the aloe vera is concentrated aloe vera and wherein the composition comprises from about 2 mg/mL to about 20 mg/mL concentrated aloe vera.

15. The composition of claim 1, wherein the composition further comprises green tea.

16. The composition of claim 15, wherein the green tea is concentrated green tea and wherein the composition comprises from about 2 mg/mL to about 20 mg/mL concentrated green tea.

17. The composition of claim 1, wherein the composition further comprises resveratrol.

18. The composition of claim 1, wherein the composition further comprises carboxymethyl cellulose.

19. The composition of claim 1, wherein the composition further comprises xanthan gum.

20. The composition of claim 1, wherein the composition has an oxygen radical absorbance capacity (ORAC) of greater than 1000 μmol/g of the composition.

21. The composition of claim 1, wherein an ORAC value for the composition is at least 1.5 fold higher than the sum of individual ORAC values for each component of the composition.

22. The composition of claim 1, comprising from about 0.05 mg/mL to about 1.0 mg/mL superoxide dismutase.

23. The composition of claim 1, comprising from about 0.1 mg/mL to about 0.5 mg/mL superoxide dismutase.

24. The composition of claim 1, comprising from about 90 mg/mL to about 250 mg/mL soluble pre-biotic fiber.

25. The composition of claim 1, comprising from about 100 mg/mL to about 200 mg/mL soluble pre-biotic fiber.

26. A composition comprising:
   a) from about 0.005 mg/mL to about 3.0 mg/mL superoxide dismutase;
   b) from about 70 mg/mL to about 500 mg/mL soluble pre-biotic fiber selected from soluble corn fiber, inulin, Guar gum, polysaccharide fiber, galactopolysaccharides, fructo-oligosaccharides, lactulose, digestion-resistant starch, xylo-oligosaccharides and isomalto-oligossacharides; and
   c) at least two fruit juices selected from pomegranate juice, Concord grape juice, blueberry juice, dark sweet cherry juice, sour cherry juice, goji berry juice and acai berry juice;
   wherein the composition is in the form of a gel.

27. The composition of claim 26, wherein the soluble pre-biotic fiber is soluble corn fiber.

28. The composition of claim 27, wherein the soluble corn fiber is digestion-resistant maltodextrin.

29. The composition of claim 26, further comprising carboxymethylcellulose.

30. The composition of claim 26, further comprising xanthan gum.

31. The composition of claim 26, comprising from about 0.05 mg/mL to about 1.0 mg/mL superoxide dismutase.

32. The composition of claim 26, comprising from about 0.1 mg/mL to about 0.5 mg/mL superoxide dismutase.

33. The composition of claim 26, comprising from about 90 mg/mL to about 250 mg/mL soluble pre-biotic fiber.

34. The composition of claim 26, comprising from about 100 mg/mL to about 200 mg/mL soluble pre-biotic fiber.

* * * * *